US00PP23559P3

(12) United States Plant Patent
Whitcomb et al.

(10) Patent No.: US PP23,559 P3
(45) Date of Patent: Apr. 23, 2013

(54) CRAPEMYRTLE PLANT NAMED 'WHIT IX'

(50) Latin Name: *Lagerstroemia indica*
Varietal Denomination: WHIT IX

(75) Inventors: Carl E. Whitcomb, Stillwater, OK (US); Andrew C. Whitcomb, Stillwater, OK (US)

(73) Assignee: Lacebark, Inc., Stillwater, OK (US)

( * ) Notice: Subject to any disclaimer, the term of this patent is extended or adjusted under 35 U.S.C. 154(b) by 113 days.

(21) Appl. No.: 13/066,110

(22) Filed: Apr. 6, 2011

(65) Prior Publication Data

US 2012/0260375 P1 Oct. 11, 2012

(51) Int. Cl.
*A01H 5/00* (2006.01)

(52) U.S. Cl. ..... Plt./252

(58) Field of Classification Search ..... Plt./252
See application file for complete search history.

(56) References Cited

U.S. PATENT DOCUMENTS

| | | | | |
|---|---|---|---|---|
| PP10,342 | P * | 4/1998 | Sorensen | Plt./360 |
| PP14,438 | P2 | 12/2003 | Whitcomb | |
| PP14,975 | P3 | 7/2004 | Whitcomb | |
| PP16,616 | P2 | 6/2006 | Whitcomb | |

* cited by examiner

*Primary Examiner* — June Hwu
(74) *Attorney, Agent, or Firm* — Jeffrey L. Streets; Streets & Steele

(57) ABSTRACT

A new and distinct variety of crapemyrtle, *Lagerstroemia indica*, particularly distinguished by having a much branched, near globular growth habit, and a near constant show of sterile, ruby red flowers from bright crimson flower buds during the growing season. Because the plant is sterile, old flowers stay showy longer, and new flower buds form in the same positions as flowers that age and fall away. Inflorescences are only between 1.5 and 6 inches long but are produced in great numbers across the outer surface of the network of branches.

5 Drawing Sheets

Genus, species: *Lagerstroemia indica.*
Varietal denomination: 'WHIT IX'.

BACKGROUND OF THE INVENTION

1. Field of the Invention

The present invention relates to a new and distinct variety or cultivar of the ornamental shrub, *Lagerstroemia indica*, commonly known as crapemyrtle.

2. Description of the Related Art

Crapemyrtle is native to eastern China and was introduced into North America in the late 1700's. Since then this popular ornamental shrub has been grown extensively across the southern half of the continent. Over the years, seedlings of *Lagerstroemia indica* have been selected and introduced into the market with different growth habits and flower colors. In addition, hybrids between *L. indica* and *L. fauriei* have been selected to add additional features, particularly more striking bark color.

An assortment of methods has been utilized to develop improved varieties of crapemyrtle and several of those varieties have had U.S. Plant Patents issued. For example, U.S. Plant Pat. Nos. 4,182, 4,183, 4,184 and 4,185 disclose and claim a series of four new varieties of *Lagerstroemia indica* produced by crossing previously known varieties. Each of these varieties was characterized as having a weeping growth habit at maturity. U.S. Plant Pat. No. 5,302 also discloses a new variety of crapemyrtle exhibiting a weeping growth habit at maturity.

U.S. Plant Pat. Nos. 6,365 and 6,383 disclose varieties of crapemyrtle derived from seedlings treated with a mutation-inducing chemical. It is generally known that sodium azide, colchicines and other chemicals are capable of producing plant mutations. Since one or more of the great, great grandparents of the new variety of crapemyrtle was treated with one of these compounds, it is possible that the present invention may be a chemically induced mutation.

The new variety of crapemyrtle claimed herein, which has been given the cultivar name 'WHIT IX' was selected from a block of about 14,000 seedlings planted in 2002. Parents of these 14,000 seedlings were 12, 13 or 14 generations removed from the original single seedling parent used to begin this crapemyrtle breeding program.

The specific identity of the parent of the present invention has been lost due to hail destroying the aluminum identification label during year 5 and, because the plant had yet to flower, no timely effort was made to reestablish the specific parent. The present invention did finally flower during the $6^{th}$ growing season, however, which is highly unusual. By contrast, nearly all crapemyrtle seedlings in our selection program flower the second or third year, while only a very few seedlings never flower at all.

This new and distinct crapemyrtle was asexually reproduced by rooting softwood cuttings taken from the original 'WHIT IX' plant near Stillwater, Okla. The asexually reproduced plants show the unique features that characterize this crapemyrtle, thereby indicating that the unique features of this plant are stable through its successive generations of asexual reproduction. Softwood cuttings taken from our new variety of crapemyrtle were successfully rooted under intermittent mist. Subsequent cuttings from plants produced from previous cuttings of the 'WHIT IX' original parent have been rooted and are identical to the original plant. Growth, flowering, flower and foliage color and capacity to rebloom on old inflorescences remain consistent with the parent.

SUMMARY OF THE INVENTION

The plant of the present invention is a new and distinct variety of crapemyrtle, *Lagerstroemia indica*, which has been given the cultivar name 'WHIT IX' and is characterized by a much branched growth habit with moderate vigor that may reach a height and width of about 6 to 8 feet if left unpruned. The original 'WHIT IX', now 8 years old, is about 5' 2" tall by 5' 6" wide.

Leaves of the plant emerge dark red-purple and soon change to dark green. Mature leaves are smaller and more pointed than is typical of the species. Twigs of current season growth begin dark purple and soon change to green.

Inflorescences are between about 1.5 to 6 inches long and between 2.5 and 4 inches wide. Flower buds are crimson. Individual flowers are ruby red with little flower color change between first opening until flowers age and drop cleanly. Density of the flower petals obscures most stamens. Many stamens remain congested in the partially open bud scales and never emerge, however the few stamens that emerge are bright yellow.

Flowers are sterile. Occasionally at the end of the growing season, a small seed capsule may develop; however, to date they have contained no seeds.

Each inflorescence typically produces a full flower show, then as the flowers age and fall, new flower buds quickly form in the locations of the previous flowers. This unique feature creates a near continuous show of flowers during the growing season when not checked by drought or other environmental or cultural problem. Flowering typically begins in late June in North Central Oklahoma and flowering continues until frost.

The photographs of FIGS. 1 to 5 were all taken while the crapemyrtle plant 'WHIT IX' was 8 years old.

DETAILED BOTANICAL DESCRIPTION.

The following botanical description is of the new and distinct cultivar of crapemyrtle, *Lagerstroemia indica*, which has been given the cultivar name 'WHIT IX'. Specific color designations set forth by number designations are in accordance with The Royal Horticultural Society Colour Chart (1966). General color recitations are consistent with ordinary American color terminology.

The crapemyrtle 'WHIT IX' has not been observed under all possible environmental conditions. It is to be understood that the phenotype may vary significantly with variations in environment such as soils, temperature, light intensity and length of day without differences in the genotype of the plant. The following botanical characteristics and observations are taken from the plant when grown under normal outdoor conditions in north central Oklahoma. Unless otherwise noted, the following description is of the original parent plant, about 8 years old, growing in a field near Stillwater, Okla., but is also consistent with plants ranging from a few months to 18 months growing in containers in north central Oklahoma.

The plant:

*Type*.—Deciduous woody shrub with multiple stems and dense branching.

*Classification*.—Crapemyrtle, *Lagerstroemia indica*.

Figure 5:
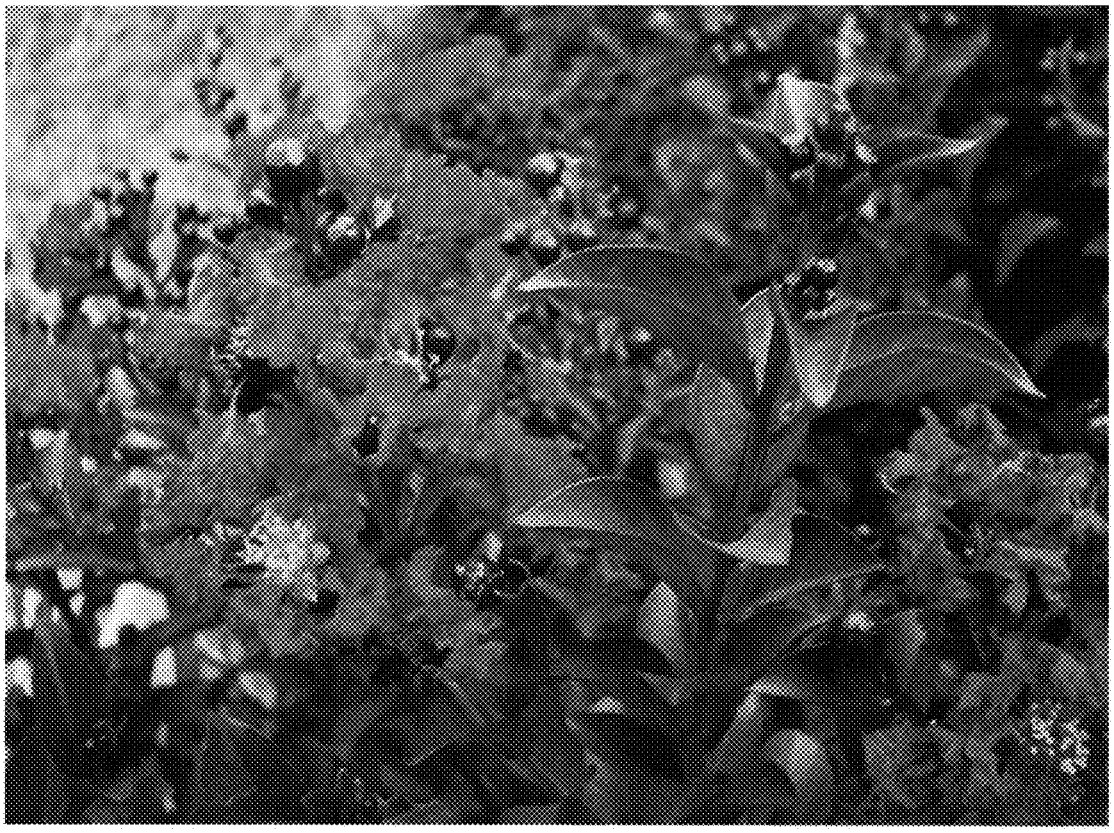
FIG. 5 is a full color photographic view of an inflorescence with flowers at left, with the occasional flower showing yellow stamens and a new stem showing wine new foliage, the color transition of leaves with age, and color of a new stem.

*Growth habit*.—The plant is a moderate grower with prolific branching. Vegetative growth is moderate in spring and continues until early summer when flowering begins. Unlike other crapemyrtle varieties from this breeding program, such as the crapemyrtles described in U.S. Plant Pat. Nos. 10,296 and 11,342 which produce little new growth once flowering begins, 'WHIT IX' of the present invention typically produces some new vegetative growth adjacent to full flowering inflorescences as shown in FIG. 5.

*Origin*.—An open pollinated cross in a crapemyrtle selection/breeding program near Stillwater, Okla.

*Propagation*.—The plant is easy to propagate from softwood cuttings, with the distinguishing characteristics of the asexually propagated offspring remaining identical to the parent.

Figure 1:
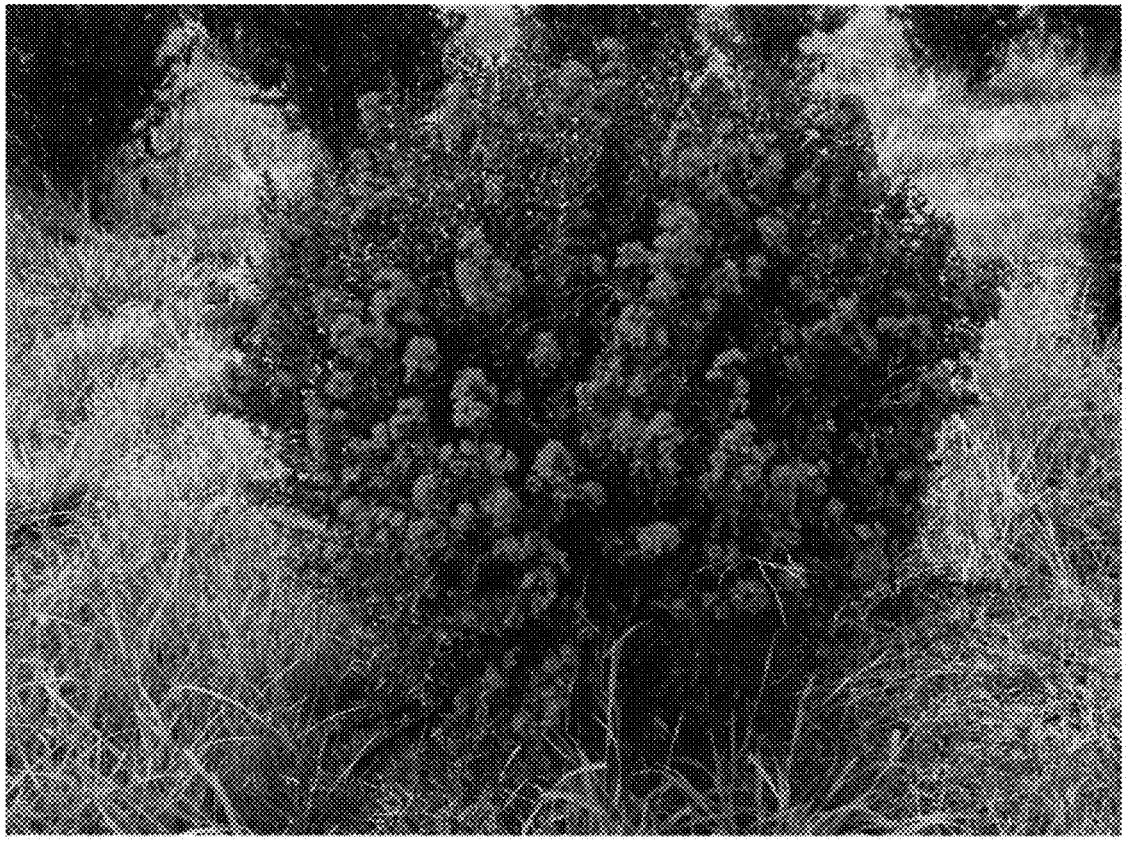
FIG. 1 is a full color photographic view of our new crapemyrtle plant 'WHIT IX', showing its growth and flowering habit near Stillwater, Okla., at age 8 years.

*Size and shape*.—The original parent has a height of 5 ft. 2 in. after 8 years of growth in the field and a width of 5 feet, 6 inches forming a dense rounded shrub as shown in FIG. 1. Based on the growth rate of the original 'WHIT IX', it is estimated that the mature height may be between about 6 and 8 feet tall with a spread of 7 to 9 feet.

*Hardiness*.—The new variety of crapemyrtle has withstood temperatures of about 8 degrees F. with no injury.

*Pests and disease*.—The foliage has been very resistant to powdery mildew and *Cercospora* leaf spot.

Figure 3:
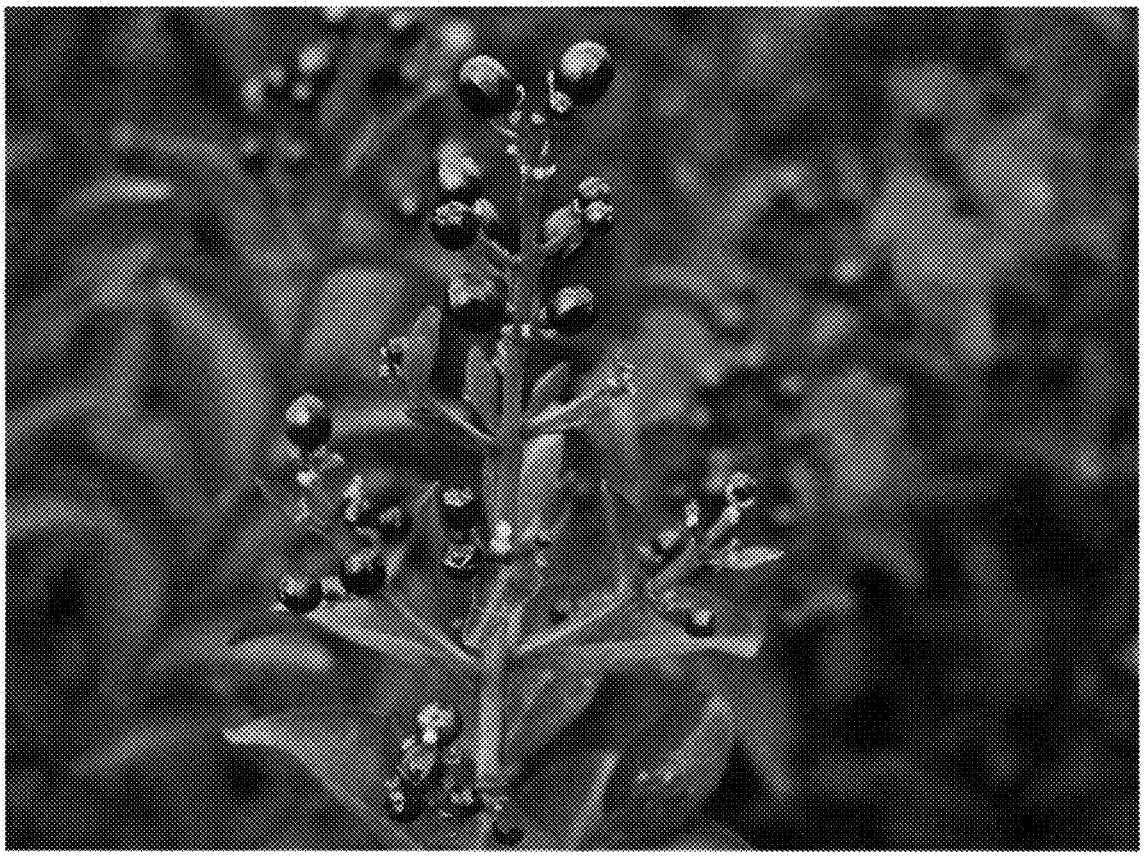
FIG. 3 is a full color photographic view of flower buds developing on an inflorescence that has already produced one set of flowers.

The flowers:

*Blooming period*.—Blooming begins in late June and continues into October in North Central Oklahoma. This flowering period is longer than most seedlings and cultivars of crapemyrtle known to me. Flowering continues during periods of intense and prolonged heat as long as moisture is available. Because the plant is sterile, flowers remain showy longer and after flowers age and fall from positions in the inflorescence, new flower buds are produced in the same location as shown in FIG. 3. Typically, four or more sets of flowers are produced on each inflorescence. This unusual flower production makes the flower show almost continuous and removes the peaks and valleys of flower show of conventional crapemyrtle. Individual flowers typically remain attractive for 12 to 18 days unless moisture is severely limiting.

Figure 2:
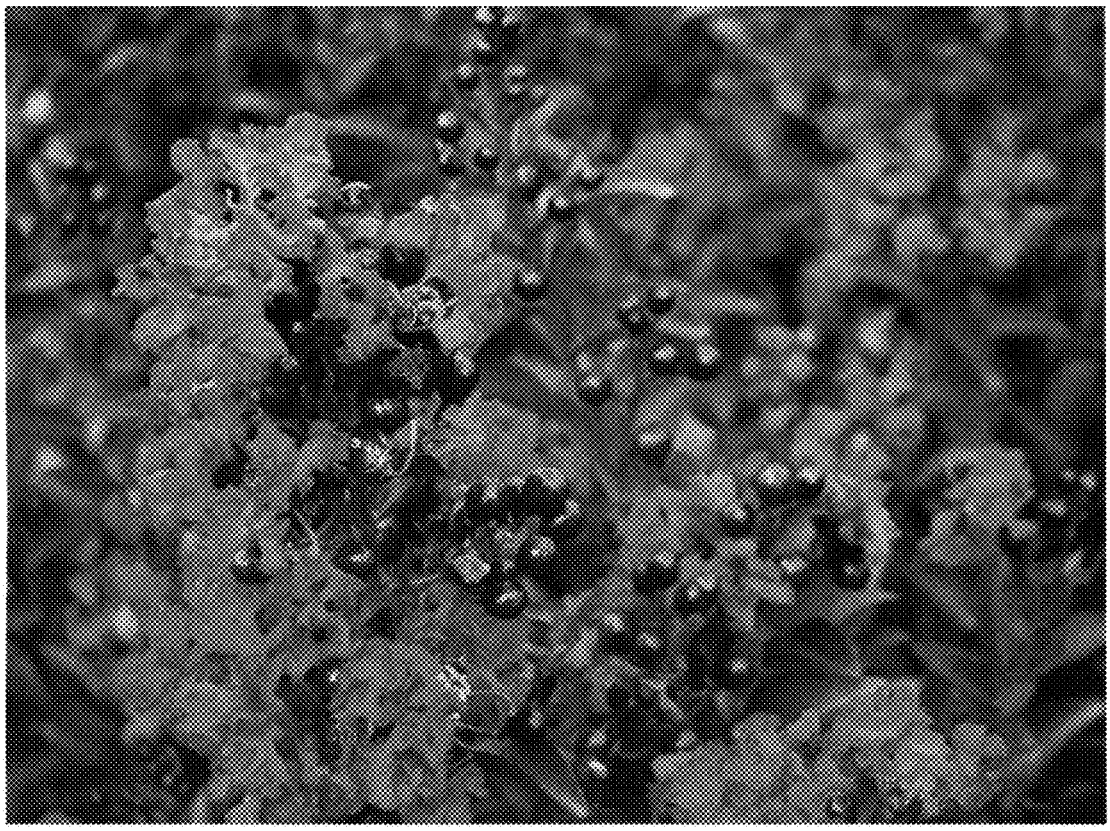
FIG. 2 is a full color photographic view of an inflorescence in nearly full flower just left of center and another with crimson flower buds to the right.

*Petals*.—Blades of individual newly opened petals (expanded apical portion) are ruby red (59 B or C) and become slightly darker (59 A) with age. Overall the flower petal shape is more or less orbicular with an uneven and irregular undulating margin and about ⅜ to ½ inch across. The petal claw (the narrow stalk-like basal portion of the petal) is also ruby red (59 B or C) and about ¼ inch long. The flower petals, typically 6, but occasionally 5, open only partially on most flowers creating a dense cluster of petals as shown in FIG. 2, with only an occasional flower opening conventionally to expose the stamens as shown in FIG. 5. Stamens range from 12 to 30 in the few flowers with visible stamens. When anthers are present they are about 1/16 inch long, yellow, approx 15-A. Filaments are approx. ⅛ inch long. Most flowers have no anthers, only an entangled mass of filaments. As the flowers age, the entire perianth of petals and sepals typically fall cleanly as a unit from the inflorescence without discoloring or becoming unattractive.

*Inflorescences*.—The inflorescences are panicles from about 1.5 to 6.0 inches long and from 2.5 to 4 inches wide and contain from 20 to 250 buds or flowers. The stocks of inflorescences (peduncle) exposed to full sun are purplish (187-A or B mid summer with max light intensity or 177 A, B, or C late in the season when nights begin to cool) as initial flower buds are forming. However, after being partially or mostly shaded by flowers for 12 to 18 days, stocks are lighter in color and range from about (187-D to 186-A,B,C or D) as shown in FIG. 3. Because of the complex and irregular branching of the inflorescence in FIG. 3, precise assignments of colors to structural parts is difficult.

*Stamens*.—An occasional flower has distinct yellow stamens (15-A), but more common are a complex of twisted and deformed stamens mostly retained in the flower bud as shown in FIG. 2.

*Sepals*.—There as six sepals per bloom, each having the shape of one-sixth of a sphere and each about 5/16 to 7/16 long.

*Buds*.—Unopened flower buds are round with six distinct lines of dehiscence where they split to allow flower petals to expand. Bud size increases with age to typically between about 3/16 and 5/16 inch diameter. The unopened flower buds are typically dark crimson (187-A) in direct sun to slightly lighter (187-B or C) where buds are partially shaded.

*Seeds*.—The plant is sterile. Late in the season and with the first frost, it appears that small seed capsules are present, but these are in fact, flower buds that have dried and partially opened.

Figure 4:
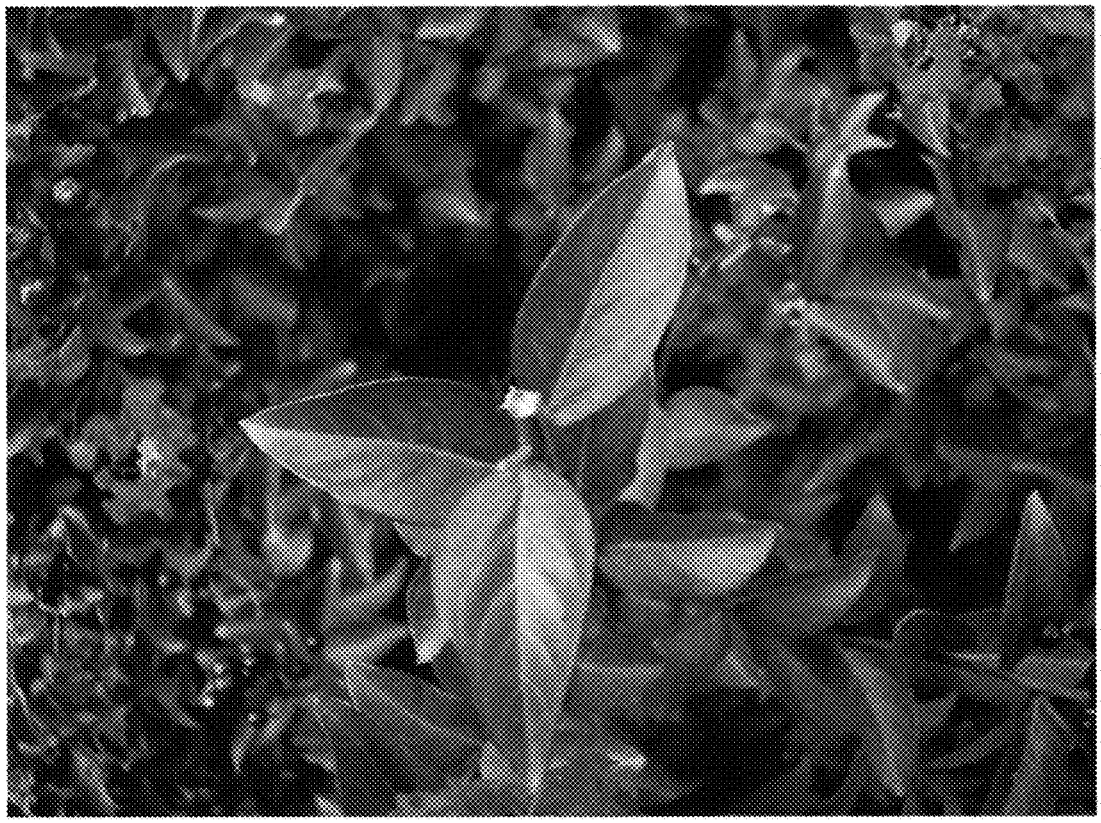
FIG. 4 is a full color photographic view of mature leaf shape, color and purplish leaf margin.

The foliage:

*Leaf shape*.—The leaf shapes range from ovate and acute at the tip to broadly lanceolate as shown in FIG. 4. The leaf petiole is typically absent or very short and not distinct. However, when a slight petiole is present, it is approximately 147-A, but there is not good match with the R.H.S. Colour Chart.

*Leaf color*.—The upper and lower leaf surfaces of new leaves emerge glossy dark purple, grayed-purple group (187-A or B) and remain so for only a few days with a gradual transition to green with age and maturity (147-A or B) and with a slight wine-green leaf margin (no color match among R.H.S. Colour Chart). This plant is typically still in full flowering mode with the arrival of the first frost, such that there is no fall color.

*Leaf texture*.—Mature leaves are smooth on both upper and lower surfaces, thick and leathery.

*Leaf size*.—The leaf size is smaller than the species average, varying from between about 1.0 and about 2.5 inches long and between 0.5 and 1.25 inches wide, with the widest point below the center.

The branches and bark:

*Branch color*.—The current season's stems, exposed to direct light are purple, grayed-purple (187-A or B). As stems age there is a transition to a lighter grayed-purple (187-B, C or D) and finally to medium brown (177-B,C or D).

*Branch length*.—The branch length is dependent upon the growing conditions of the plant, typically ranging from between about 4 to 10 inches.

*Branch diameter*.—The diameter of a current season's growth ranges from between about 3/32 to 9/32 inch.

*Bark*.—The young bark of branches from ⅛ to ¾ inch stem diameter is typical of *L. indica* species (about 199-C or D on ½ to ¾ inch diameter stems to about 200-D on one year old stems). Unlike a typical crape-myrtle, the base of the 8 year old stems has yet to begin to exfoliate.

We claim:

1. A new and distinct variety of crapemyrtle plant, *Lagerstroemia indica*, substantially as illustrated and described.

* * * * *